US007969560B2

(12) United States Patent
Kostuch et al.

(10) Patent No.: US 7,969,560 B2
(45) Date of Patent: Jun. 28, 2011

(54) OPTICAL PROPERTY SENSOR

(75) Inventors: Gregory D. Kostuch, Mahtomedi, MN (US); David L. Hofeldt, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/663,788

(22) PCT Filed: Jul. 1, 2008

(86) PCT No.: PCT/US2008/068913

§ 371 (c)(1), (2), (4) Date: Dec. 9, 2009

(87) PCT Pub. No.: WO2009/014866

PCT Pub. Date: Jan. 29, 2009

(65) Prior Publication Data

US 2010/0188651 A1 Jul. 29, 2010

(51) Int. Cl.
*G01N 21/00* (2006.01)

(52) U.S. Cl. ........................... 356/73; 356/337; 356/425

(58) Field of Classification Search .................. 356/236, 356/402–425, 432–444, 445–448, 337–343, 356/73

See application file for complete search history.

(56) References Cited

U.S. PATENT DOCUMENTS 4,687,943 A 8/1987 Bowen et al.
5,712,709 A 1/1998 Task et al.
5,760,890 A 6/1998 Lex et al.
6,091,492 A 7/2000 Strickland et al.
6,122,042 A 9/2000 Wunderman et al.
6,628,355 B1 * 9/2003 Takahara ........................ 349/42
7,495,763 B2 * 2/2009 Palumbo ........................ 356/337
2006/0256338 A1 11/2006 Gratton et al.
2007/0046944 A1 3/2007 Ghil et al.

FOREIGN PATENT DOCUMENTS

GB 1078181 A 8/1967
JP 63075537 A 4/1988
JP 2002310902 A 10/2002
JP 2006153738 A 6/2006

OTHER PUBLICATIONS

Beek et al., "In vitro double-integrating-sphere optical properties of tissues between 630 and 1064nm", Phys. Med. Biol., vol. 42, No. 11, (Nov. 1997) pp. 2255-2261.

Pickering et al., "Optical property changes as a result of protein denature in albumen and yolk", J. Photochem. Photobiol. B: Biol., vol. 16, No. 2, (Oct. 1992) pp. 101-111.

(Continued)

*Primary Examiner* — Gregory J Toatley
*Assistant Examiner* — Iyabo S Alli
(74) *Attorney, Agent, or Firm* — Daniel R. Pastirik; James A. Baker

(57) ABSTRACT

An apparatus that can measure both haze and clarity on a web moving at conventional manufacturing speeds. The apparatus uses an integrating sphere and a novel mirror arrangement. With this arrangement, the invention can utilize a calibration curve created using known samples over the range of measurement desired to convert in real time, and the response of two photo detectors that measure the wide and low angle scattering signals, to deduce the desired optical property values. This approach significantly increases the speed and response of sensor and enables either on-line single point or full web scanning for uniformity measurement and control.

7 Claims, 1 Drawing Sheet

OTHER PUBLICATIONS

Shen, et al., "Characterization of mar/scratch resistance of coatings with a Nano-indenter and a scanning probe microscope", Tribology International, vol. 39, No. 2, (Feb. 2006), pp. 146-158.

European Search Report from European application No. 08772310.2-2204, dated Nov. 19, 2010, 9 pp.

ASTM D1003, ISO 13468, Nov. 1, 2007.

* cited by examiner 45a 45b

OPTICAL PROPERTY SENSOR

TECHNICAL FIELD

The present invention is related to a sensor for optical properties. It is particularly adapted to provide information from moving webs in real time.

BACKGROUND

In the manufacturing of, e.g. optical films, it is sometimes necessary to control one or more optical properties quite closely to make acceptable product. For example, the properties of transmission haze, clarity, and transmittance, are frequently of great interest when making films for, e.g. optical panel displays.

Transmission haze is a term used in the art to describe the wide angle scattering of visible light as it goes through a film. Percent haze is generally defined within various standard test methods (e.g., ASTM D1003, ISO 13468) as the ratio of the diffuse light transmittance to the total transmittance through a film or substrate. More specifically, transmission haze is defined as that component of light that is diffusely scattered outside a 2.5 degree angle with respect to a collimated light beam as it transmits orthogonally through the substrate to be measured. Clarity is the optical term used to describe the low angle light scattering that is found within the 2.5 degree angle and transmittance is defined as the ratio of transmitted light through a substrate to the total light incident the film.

Techniques for the measurement of haze and other optical properties are known, and the art describes devices to make such measurements, such as those commercialized by BYK-Gardner GmbH for off-line use. While useful for an analytical lab, these devices are difficult to utilize on-line in manufacturing because of slow response time due to the need to position and remove a cover at the exit port of an integrating sphere for each haze measurement to obtain the total transmitted light through a film as required by ASTM D1003 standard protocol. To make a standalone, absolute measurement of haze, some method to determine total transmitted light through the film is required.

OCS Gmbh (Optical Control Systems) in Germany has developed an on-line sensor based on the same ASTM D1003 standard with the same constraints as the BYK GARDNER device. While suitable for some applications where line speeds are slow, this design only measures haze, and is only configured as a single point measurement. Moreover, the device is big and bulky making it difficult to utilize and incorporate into a scanning frame for on-line uniformity measurement.

The art also describes a portable haze measurement device used to test windscreen material for aircraft. However, this design utilizes a specific wavelength laser source, which may present a problem for materials that scatter more at other wavelengths.

There is an unmet need for an apparatus capable of measuring both haze and clarity over the width of a web moving at commercially viable line speeds.

SUMMARY

In one aspect, the present invention provided an apparatus for sensing at least one optical property of a sample, the apparatus comprising:

a source of light that is substantially collimated along an axis;

an integrating sphere having a light inlet, an on-axis aperture, and an off-axis aperture;

a scatter sensor positioned at the off-axis aperture;

a light trap positioned adjacent the on-axis aperture, the light trap having a transmittance sensor disposed within;

a parabolic mirror positioned so as to reflect light passing through the on-axis aperture towards the transmittance sensor; and an analysis circuit for receiving intensity information from the scatter sensor and the transmittance sensor and reporting a value correlated to the optical property of a sample placed between the source of light and the integrating sphere.

In another aspect, the invention provides a method of sensing at least one optical property of a sample, the method comprising:

(A) providing a sensor suite, the sensor suite comprising (i) an integrating sphere having a light inlet having an axis, an on-axis aperture, and an off-axis aperture;

(ii) a scatter sensor positioned at the off-axis aperture;

(iii) a light trap positioned adjacent the on-axis aperture, the light trap having a transmittance sensor disposed within; and (iv) a parabolic mirror positioned so as to reflect light passing through the on-axis aperture towards the transmittance sensor;

(B) directing a substantially collimated beam of light along the axis, through the sample and into the light inlet; and (C) analyzing intensity information from the scatter sensor and the transmittance sensor and reporting a value correlated to the optical property of the sample.

In describing the embodiments of the invention, certain terms will be understood to have their ordinary meaning. For clarity, the following terms shall have the meaning set forth herein:

"ASTM" refers to ASTM International (formerly know as the American Society for Testing and Materials) and to test methods licensed by ASTM International (e.g., ASTM D1003).

"ISO" refers to the International Organization of Standardization, an international body of technical standards for various industries and to test methods licensed by ISO (e.g., ISO 13468).

"LED" refers to a light emitting diode.

DESCRIPTION OF THE DRAWINGS

In describing embodiments of the invention, reference is made to the Figures in which structural features are identified using reference numerals, and wherein.

DETAILED DESCRIPTION

Figures 1, 2:
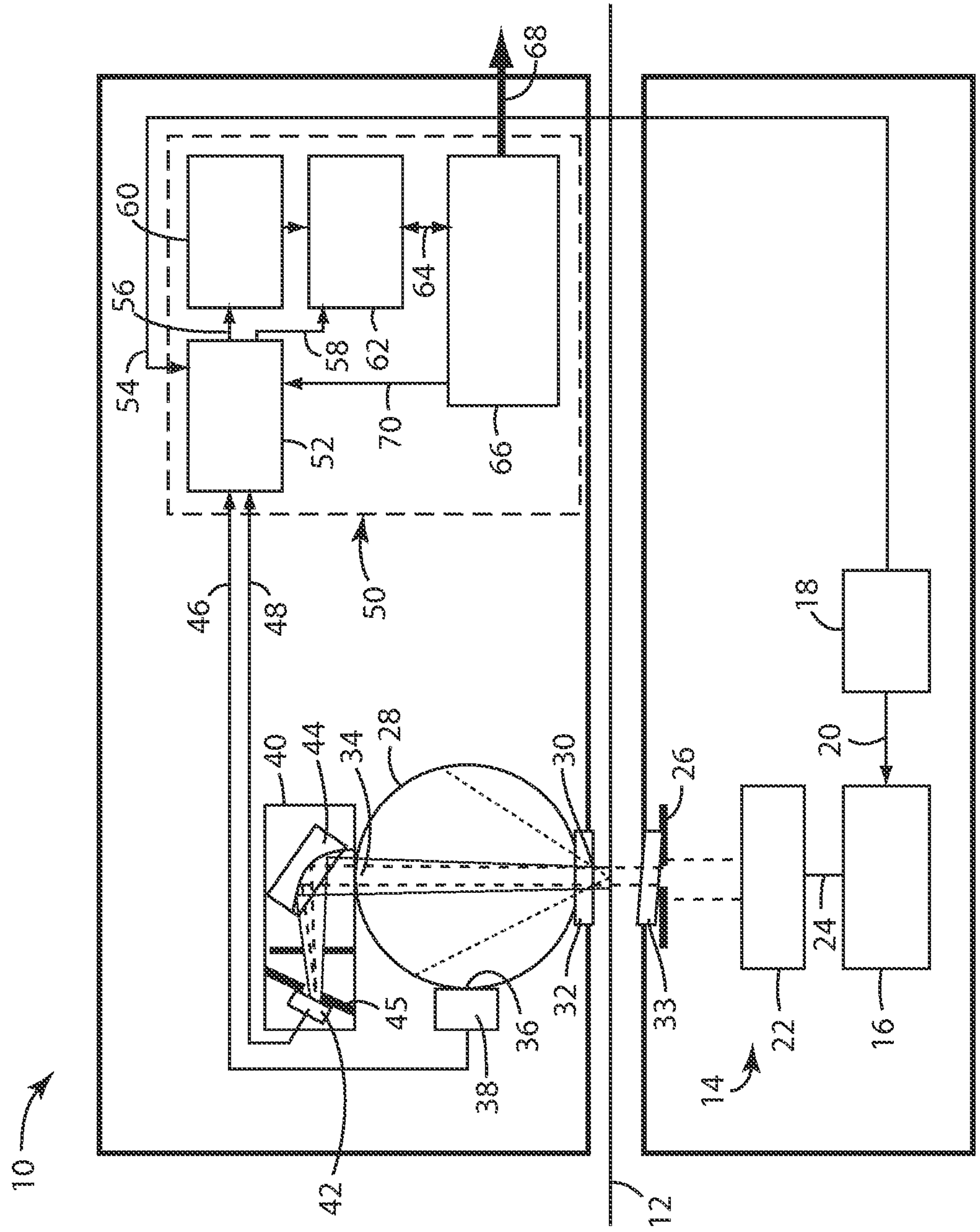
FIG. 1 is a block diagram of an apparatus according to an embodiment of the invention.
FIG. 2 is a top plan view of two alternate versions of an aperture plate that may be used in connection with an apparatus according to FIG. 1.

The invention provides an apparatus that can measure both haze and clarity on a web moving at conventional manufacturing line speeds. The present invention utilizes an integrating sphere and a novel mirror arrangement. With this arrangement the invention can utilize a calibration curve created using known samples selected to cover the range of measurement desired to deduce in real time the desired optical property values. In some embodiments, expedients to compensate for longer term system variations (such as light source intensity drift), built-in haze, clarity, and/or transmittance standards are periodically measured. This technique is fast, robust, and demonstrates good and repeatable correlation to off-line tools built to measure to the accepted protocols. This approach significantly increases the speed and response of sensor and enables either on-line single point or full web scanning for uniformity measurement and control.

In one aspect, the invention provides an apparatus for sensing at least one optical property of a sample. The apparatus includes a source of light that is substantially collimated along an axis. An integrating sphere is present with a light inlet aligned with that axis, and an on-axis aperture and an off-axis aperture. A scatter sensor is positioned at the off-axis aperture. A light trap is positioned adjacent to the on-axis aperture, and this light trap has a transmittance sensor disposed within. A parabolic mirror is positioned so as to reflect light passing through the on-axis aperture towards the transmittance sensor. An analysis circuit is present, which receives intensity information from the scatter sensor and the transmittance sensor and reports a value correlated to the optical property of a sample placed between the source of light and the integrating sphere.

Referring now to the Figures, FIG. 1 is a block diagram of an apparatus 10 for sensing at least one optical property of a sample 12. The apparatus 10 includes a source of light 14 to provide a light beam that is substantially collimated along an axis. The source of light may include an LED module 16 under the control of an LED driver 18 via control path 20. If the light output of the LED module 16 is not yet collimated, it is convenient to couple its output to an optical collimator 22 via fiber optic line 24.

Light from the source 14 is directed out an aperture 26 and through the sample 12. It then enters an integrating sphere 28 through light inlet 30. In some embodiments, the light inlet 30 will have a protective window 32. An optional protective window 33 may be present to protect the collimator 22. Protective window 33 may be tilted out of the plane perpendicular to the axis of the collimator 22 in order to minimize inadvertent reflections back towards the source 14.

Integrating sphere 28 includes an on-axis aperture 34 and an off-axis aperture 36. A scatter sensor 38 is positioned at the off-axis aperture 36. A light trap 40 is positioned adjacent the on-axis aperture 34, with a transmittance sensor 42 disposed within the light trap 40. A parabolic mirror 44 is positioned to reflect light passing through the on-axis aperture 34 towards the transmittance sensor 42. The dashed lines within integrating sphere 28 portray the light path of a collimated light beam through a sample 12 when no haze (diffuse scattering) exists and clarity is 100%. When clarity becomes worse (<100%), there is low angle spread of the collimated beam. When reflected off the parabolic mirror 44, a halo is projected around the focused main beam. The intensity of this halo is a function of its clarity.

Optional aperture plates 45 may be positioned within the light trap 40 adjacent to the transmittance sensor 42 so as to limit the light falling on the transmittance sensor 42 to a particular range of angles compared to the central axis of parabolic mirror 44. Referring to FIG. 2, two embodiments of aperture plate 45 that may be used in connection with apparatus 10 are illustrated. Aperture plate 45*a* only allows light that is diverging from the central axis of parabolic mirror 44 to reach transmittance sensor 42. Alternative aperture plate 45*b* is more restrictive, and tends to allow only light that is being focused by parabolic mirror 44 towards its central axis to reach transmittance sensor 42. An enlarged version of aperture plate 45*b* may also be used so as to allow both the divergent and focused light reflecting off the parabolic mirror 44 to reach transmittance sensor 42. The version of aperture plate 45 used is significant as it defines which optical property is to measured. Whereas aperture plate 45*a* is best suited to measure clarity, aperture plate 45*b* is used for measuring various forms of transmittance.

Referring again to FIG. 1, information from the scatter sensor 38 and the transmittance sensor 42 is sent via signal lines 46 and 48 respectively to an analysis circuit 50. The analysis circuit 50 receives the intensity information and reports a value correlated to the optical property of interest of sample 12. The analysis circuit 50 may advantageously include a sensor amplifier 52 to condition the signals on signal lines 46 and 48. In order for analysis circuit 50 to better reject the influence of ambient light on the measurement, in may be convenient for the LED driver 18 to chop the light emitted by the LED module 16. In such embodiments, information about the chopping is conveyed from LED driver 18 to the sensor amplifier 52 via signal line 54.

Conditioned signals from the sensor amplifier 52 are conveyed on signal lines 56 and 58 to a lock-in amplifier 60 and an analog-to-digital (A/D) converter 62. The lock-in amplifier 60 acts to convert a chopped signal (if chopping is being used) back into continuous form. The A/D converter 62 adapts the signals to be transmitted on signal line 64 to a microcomputer 66. Once this has been done, the signals can be correlated to the optical property of interest, and values reported in any convenient manner (represented as signal line 68). In some convenient embodiments, signal gain control information is fed to the sensor amplifier 52 from microcomputer 66 along signal line 70.

Microcomputer 66 may be obtained commercially and is of sufficient capacity to process the incoming signal and compare it to a standard calibration curve for the optical property of interest. The apparatus 10 may be calibrated using standard materials similar to those being measured and having premeasured optical properties as determined by standard test methods on conventional off-line instruments such as the instruments available from BYK-Gardner GmbH for off-line use. Calibration curves may be prepared using liner regression techniques, for example, and the calibration data may be stored in the microcomputer to be utilized in computing the optical properties of interest over the width of a moving web traveling at commercially viable line speeds. The creation of such standard curves is within abilities of a person of ordinary skill in the art.

Example

An apparatus according to the present invention was prepared generally as illustrated in FIG. 1. This embodiment was particularly suited to measure an indefinite length web, and featured two sturdy aluminum enclosures having a passage between them for the transit of the web. In one enclosure was an aperture to which was mounted an optical collimator commercially available as Model #HPUCO-23-400/700-M-25AC from OZ Optics of Ontario, Canada. This optical collimator was connected to an LED module with a pigtailed fiber commercially available as LED Pigtail LuxeonIII Star WHI 400/430 0.37NA 0.5 m FC/PC from Doric Lenses of Quebec, Canada. The LED driver was a custom circuit that delivered constant current to the LED when it was turned on. This driver was set to a chopping frequency of 9 kHz as a measure to limit the influence of ambient light on the measurement of the film. A thin glass window was mounted adjacent the aperture opposite the collimator whose normal was tilted 3 degrees from the axis of the collimator.

In the second enclosure opposite from the aperture and the collimator, an integrating sphere commercially available as Model # 4P-GPS-040-SF from Labsphere, Inc. of North Sutton, N.H. was mounted with its 1 inch diameter light inlet aligned with the axis of the collimator. A thin glass window was mounted adjacent the light inlet. The integrating sphere had a 0.5 inch diameter on-axis aperture opposite the light inlet, and a 0.5 inch diameter off-axis aperture positioned at approximately the "equator" if the light inlet and the on-axis aperture were considered the "poles". A scatter sensor commercially available as Model # PIN10DP from UDT Sensors Inc. of Hawthorne, Calif. was positioned at the off-axis aperture.

A light trap constructed of sheet metal was positioned at the on-axis aperture of the integrating sphere. A transmittance sensor commercially available as Model # PIN-10DP from UDT Sensors Inc. of Hawthorne, Calif., was positioned within the light trap. A parabolic mirror, having a focal length of 2 inches, and commercially available as Model # 50329AL from Newport Corporation of Irvine, Calif., was positioned within the light trap to focus the light emerging from the on-axis aperture towards the transmittance sensor. Optional aperture plates as shown in FIG. 2, were positioned within the light trap adjacent the transmittance sensor.

A custom signal conditioning amplifier was located in the second enclosure with connections to a lock-in amplifier commercially available as Model # LIA-BV-150-L from Electro Optical Components, Inc. of Santa Rosa, Calif., an A/D amplifier commercially available as Model #DM6420 HR-1 from RTD Embedded Technologies, Inc. of State College, Pa., and an embedded PC commercially available as Model #Netsock/415 from Micro/Sys of Montrose, Calif.

While the invention has been particularly shown and described with reference to various embodiments thereof, it will be understood by those skilled in the art that various other changes in the form and details may be made therein without departing from the spirit and scope of the invention.

What is claimed is:

1. An apparatus for sensing at least one optical property of a sample, comprising:

a source of light that is substantially collimated along an axis;

an integrating sphere having a light inlet, an on-axis aperture, and an off-axis aperture;

a scatter sensor positioned at the off-axis aperture;

a light trap positioned adjacent the on-axis aperture, the light trap having a transmittance sensor disposed within;

a parabolic mirror positioned so as to reflect light passing through the on-axis aperture towards the transmittance sensor; and an analysis circuit for receiving intensity information from the scatter sensor and the transmittance sensor and reporting a value correlated to the optical property of a sample placed between the source of light and the integrating sphere.

2. An apparatus according to claim 1 wherein the source of light comprises an LED illuminator optically coupled with an optical collimator.

3. An apparatus according to claim 2 wherein the LED illuminator is driven so as to provide light chopped at least 5 kHz.

4. An apparatus according to claim 1 further comprising a protective window associated with the optical collimator, the protective window being tilted out of the plane perpendicular to the axis.

5. A method of sensing at least one optical property of a sample, comprising:

(A) providing a sensor suite, the sensor suite comprising (i) an integrating sphere having a light inlet having an axis, an on-axis aperture, and an off-axis aperture;

(ii) a scatter sensor positioned at the off-axis aperture;

(iii) a light trap positioned adjacent the on-axis aperture, the light trap having a transmittance sensor disposed within; and (iv) a parabolic mirror positioned so as to reflect light passing through the on-axis aperture towards the transmittance sensor;

(B) directing a substantially collimated beam of light along the axis, through the sample and into the light inlet; and (C) analyzing intensity information from the scatter sensor and the transmittance sensor and reporting a value correlated to the optical property of the sample.

6. A method according to claim 5 wherein the substantially collimated beam source of light is formed by an LED illuminator optically coupled with an optical collimator.

7. A method according to claim 6 wherein the LED illuminator is driven so as to provide light chopped at least 5 kHz.

* * * * *